Figure 1:
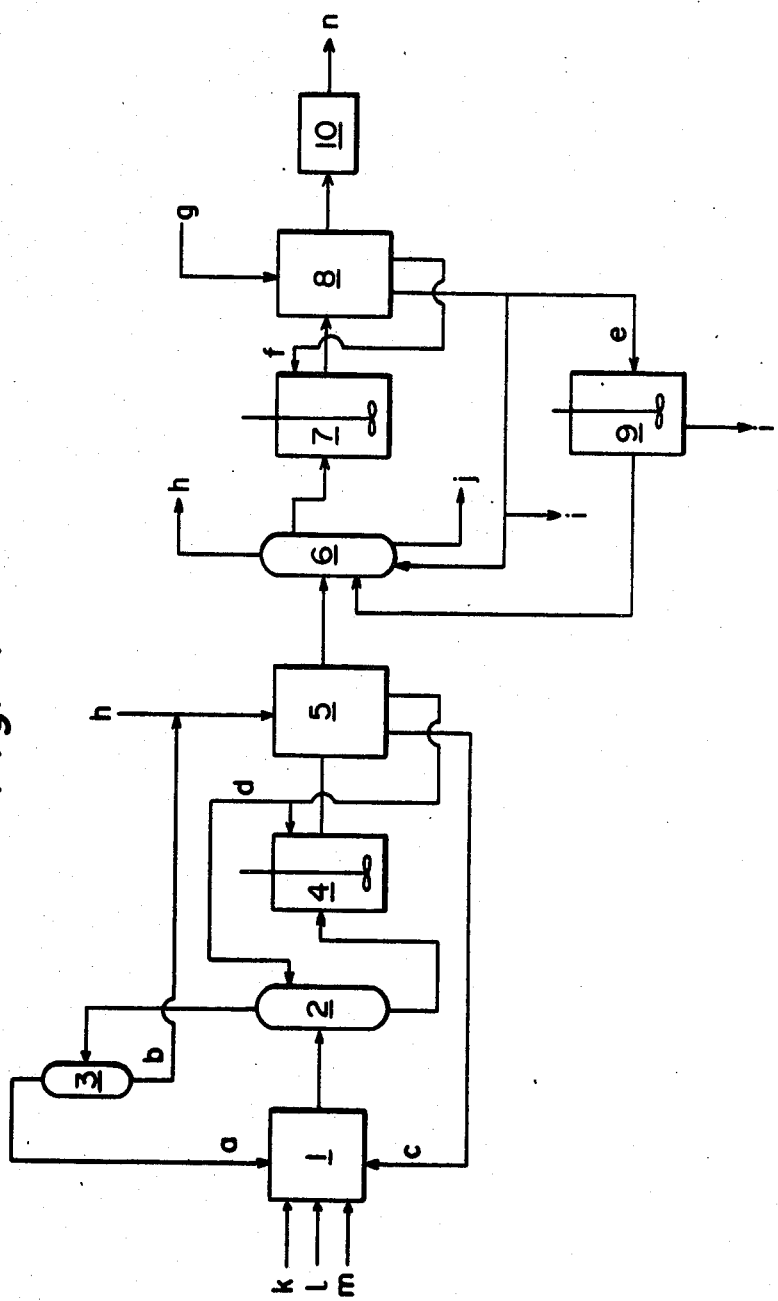

United States Patent [19]  [11] Patent Number: 4,675,444
Matsunaga et al.  [45] Date of Patent: Jun. 23, 1987

[54] PROCESS FOR PRODUCING AMINOPHENOLS

[75] Inventors: Fujihisa Matsunaga, Iwakuni; Eiji Kato, Yamaguchi; Tsuyoshi Kimura; Yoichiro Isota, both of Wakayama, all of Japan

[73] Assignees: Mitsui Petrochemical Ind., Ltd.; Honshu Chemical Ind. Co., Ltd., both of Tokyo, Japan

[21] Appl. No.: 802,182

[22] Filed: Nov. 25, 1985

[51] Int. Cl.$^4$ ............................................. C07C 85/06
[52] U.S. Cl. .................................................... 564/403
[58] Field of Search ........................................ 564/403

[56] References Cited

U.S. PATENT DOCUMENTS 4,585,896 4/1986 Harada et al. ...................... 564/403

Primary Examiner—Paul F. Shaver
Attorney, Agent, or Firm—Sherman and Shalloway

[57] ABSTRACT

A process for producing an aminophenol, which comprises
(A) a step of reacting a dihydric phenol with an aminating reagent in the liquid state under heat in the presence of water and a water-soluble catalyst,
(B) a step of removing the unreacted aminating reagent from the reaction mixture, and then precipitating the crude aminophenol from the reaction mixture from which the aminating reagent has been removed, thereby to obtain a crystallization mixture containing the crude aminophenol,
(C) a step of separating the crystallization mixture into crystals of the crude aminophenol and the reaction mother liquor containing the catalyst,
(D) a step of circulating part or the whole of the reaction mother liquor to the aminating step, and
(E) a step of washing the crude aminophenol crystals with a washing liquor to obtain the washed crude aminophenol crystals and the washing mother liquor, and thereafter separating the aminophenol from the washed crude aminophenol crystals and purifying it.

8 Claims, 1 Drawing Figure

PROCESS FOR PRODUCING AMINOPHENOLS

This invention relates to a process for producing aminophenols from dihydric phenols. More specifically, it relates to a process for producing aminophenols, which comprises reacting dihydric phenols with aminating reagents in the liquid state in the presence of water and a water-soluble catalyst, separating and recovering the aminophenols and the catalyst efficiently from the resulting mixture, and recycling the catalyst to the reaction system.

Aminophenols are useful as intermediates for the production of medicines, agricultural chemicals, dyes, rubber chemicals, additives for synthetic resins, etc. For the production of aminophenols by reacting dihydric phenols with aminating reagents such as ammonia or amines, methods have heretofore been proposed which involve using as a catalyst ammonium salt of arsenic or phosphoric acid (U.S. Pat. No. 2,376,112), a catalyst composed of an ammonium halide of copper, cobalt or nickel (Japanese Laid-Open Patent Publication No. 42829/1977), stannous chloride (Japanese Laid-Open Patent Publication No. 100427/1977), a catalyst composed of stannous chloride and ammonium chloride (Japanese Laid-Open Patent Publication No. 100428/1977), and a molybdic acid-type catalyst which gives aminophenols in higher yields and selectivities than the preceding methods (Japanese Laid-Open Patent Publication No. 108841/1980). Since, however, all of these methods use large amounts of catalysts, the economical industrial production of aminophenol by these methods requires establishment of techniques of efficiently separating the catalyst and aminophenol from the reaction mixture and recycling the recovered catalyst to the reaction system.

Investigations of the present inventors, however, have led to the discovery that the technique generally used in this field for separating the catalyst from the reaction mixture after the reaction has the following defects.

When a method is employed in which the reaction mixture is directly distilled to distill off the aminophenol and the catalyst is recovered as a distillation bottom, a considerable amount of the aminophenol remains in the distillation bottom, and the aminophenol cannot be separated with good efficiency. If one attempts to distill off the aminophenol completely, the aminophenol changes to a high-boiling compound by polycondensation reaction. Consequently, the distillation bottom becomes tarry, and it is substantially impossible to recover and re-use the catalyst.

On the other hand, when a method is employed in which the catalyst is separated from the aminophenol and recovered by extracting the reaction mixture with a solvent which does not dissolve the catalyst, the aminophenol contains high-boiling by-products which have strong coloration, and the separation of the catalyst is not always carried out with good efficiency.

The present inventors have found through the aforesaid experimental studies that these ordinary methods cannot be applied to the industrial production of aminophenol. With this background, the present inventors have extensively studied a process for industrially producing an aminophenol in which the aminophenol and the catalyst are separated from the reaction mixture with good efficiency, and the recovered catalyst is recycled to the reaction system. These investigations have led to the present invention.

It is an object of this invention to provide a process for producing aminophenols on an industrial scale.

Another object of this invention is to provide a process for producing aminophenols industrially advantageously, in which the desired aminophenols can be recovered in high yields from the reaction mixture, and the catalyst or the unreacted phenols are recovered and recycled to the reaction system.

Further objects of this invention and advantages will become apparent from the following description.

According to this invention, the above objects and advantages are achieved by a process for producing an aminophenol, which comprises (A) a step of reacting a dihydric phenol with an aminating reagent in the liquid state under heat in the presence of water and a water-soluble catalyst, (B) a step of removing the unreacted aminating reagent from the reaction mixture, and then precipitating the crude aminophenol from the reaction mixture from which the aminating reagent has been removed, thereby to obtain a crystallization mixture containing the crude aminophenol, (C) a step of separating the crystallization mixture into crystals of the crude aminophenol and the reaction mother liquor containing the catalyst, (D) a step of recycling part or the whole of the reaction mother liquor to the aminating step, and, (E) a step of washing the crude aminophenol crystals with a washing liquor to obtain the washed crude aminophenol crystals and the washing mother liquor, and thereafter separating the aminophenol from the washed crude aminophenol crystals and purifying it.

The accompanying drawing, FIG. 1, is a flow chart illustrating the continuous production of aminophenols, which is suitable for the practice of the process of this invention for producing aminophenols.

Examples of the dihydric phenol used as a reaction material in step (A) of the process of this invention include dihydric phenols having no substituent such as hydroquinone, resorcinol and catechol; and dihydric phenols having hydrocarbon groups such as 2-methylhydroquinone, 4-methylresorcinol, 5-methylresorcinol, 5-ethylresorcinol, 5-isopropylresorcinol, 5-n-butylresorcinol, 5-sec-butylresorcinol, 5-tert-butylresorcinol, 3-methylcatechol, 4-methylcatechol, 4-ethylcatechol, 4-n-propylcatechol, 4-isopropylcatechol, 4-n-butylcatechol, and 4-tert-butylcatechol. Among these dihydric phenols, the use of the dihydric phenols having no substituent is preferred. It is especially preferred to apply resorcinol or hydroquinone to the process of this invention.

Examples of the aminating reagent used in step (A) of the process of this invention include ammonia and aqueous ammonia in various concentrations; primary amines such as methylamine, ethylamine, n-propylamine, isopropylamine, n-butylamine, sec-butylamine, tert-butylamine, amylamine, hexylamine, heptylamine, octylamine, nonylamine, decylamine, dodecylamine and benzylamine; and secondary amines such as dimethylamine, diethylamine, di-n-propylamine, diisopropylamine, di-tert-butylamine, diamylamine, dihexylamine, diheptylamine, dioctylamine and didodecylamine. Of these aminating reagents, ammonia is preferred. The ammonia may be used as ammonia gas or aqueous ammonia as required. The aqueous ammonia preferably has a concentration of 10 to 60% by weight.

The proportion of the aminating reagent is usually at least 1 mole, preferably 1 to 5 moles, per mole of the dihydric phenol. When the aminating reagent is used in an amount exceeding the theoretical amount, the excess of it is recovered after the reaction and reused.

In the present invention, the reaction of the dihydric phenol with the aminating reagent should be carried out in the presence of a catalyst. The catalyst may be a known water-soluble catalyst. Examples include various metal compounds such as oxides, ammonium compounds, sulfates and ammonium salts of molybdenum, copper, antimony, vanadium, iron and nickel; and various ammonium compounds such as ammonium salts, primary amine salts, secondary amine salts, tertiary amine salts and quaternary ammonium salts, and compounds capable of forming ammonium compounds in the reaction system. Specific examples of the ammonium salts are ammonium halides such as ammonium chloride, ammonium bromide and ammonium iodide, ammonium nitrate, ammonium sulfate, ammonium phosphate and heteropolyacid or isopolyacid ammonium salts such as ammonium molybdate or ammonium tungstate. Examples of the primary amine salts or secondary amine salts are salts of the primary amines or secondary amines exemplified above as the reaction material with various acidic compounds, such as hydrofluorides, hydrochlorides, hydrobromides, hydroiodides, sulfates, nitrates, phosphates, organic acid salts, and heteropolyacid salts. Examples of the compounds capable of forming ammonium compounds in the reaction system are acidic compounds such as hydrochloric acid, hydrobromides, and heteropolyacids or isopolyacids containing molybdenum or tungsten as a component. These acidic compounds change to ammonium compounds by reaction with the aminating reagent such as ammonia, the primary amine or the secondary amine.

When an ammonium compound is used as a catalyst component, it is preferably an ammoniating reagent corresponding to the aminating reagent for the reaction substrate. For example, when ammonia is used as the aminating reagent, it is preferred to use an ammonium salt. When the primary or secondary amine is used as the aminating reagent, it is preferred to use an amine salt corresponding to it as the ammonium compound used as the catalyst component.

The particularly preferred proportion of the catalyst is usually 0.01 to 2 moles, preferably 0.05 to 1 mole, per mole of the dihydric phenol.

In step (A) of the process of this invention, water is used in an amount of usually 10 to 1000 parts by weight, preferably 10 to 500 parts by weight, per 100 parts by weight of the dihydric phenol.

The reaction of step (A) is carried out usually in an atmosphere of nitrogen. It is also possible to carry it out in an atmosphere of an inert gas such as argon and helium. The reaction temperature may vary depending upon the type of the reaction substrate, its concentration and the type and concentration of the catalyst, but is usually in the range of 170° to 350° C., preferably in the range of 180° to 300° C. The reaction is usually carried out under elevated pressures. The pressure, including the autogenous pressure attributed to the charged starting materials during the reaction and the pressurization with an inert gas which is carried out as desired before the reaction, is usually in the range of 5 to 150 kg/cm$^2$-G, preferably in the range of 10 to 50 kg/cm$^2$-G. The aminating reaction can be carried out batchwise, semicontinuously, or continuously.

The reaction mixture obtained after the aminating reaction in step (A) contains the desired aminophenol, a by-product phenylenediamine, and a trace of a coloring high-boiling material. Usually, it also contains small amounts of the unreacted dihydric phenol and the aminating reagent, and water and the catalyst.

In the next step (B) of the process of this invention, the unreacted aminating reagent is removed from the reaction mixture formed in step (A), and the crude aminophenol is precipitated to obtain a crystallization mixture of the crude aminophenol.

It is especially preferred in this invention to add the washing mother liquor obtained in step (E) to the reaction mixture from which the unreacted aminating reagent has been removed as above. As required, however, the aforesaid washing mother liquor may be added to the reaction mixture at other stages in the process, and it is also within the process of this invention that the washing mother liquor is not recycled for re-use. The advantage of adding the washing mother liquor to the reaction mixture obtained in step (A) from which the aminating reagent has been removed is that the ratio of recovery of the desired aminophenol can be increased, and the temperature and concentration of the reaction mixture to be subjected to crystallization can be adjusted. The above reaction mixture contains water and a small amount of the unreacted aminating reagent which remains unremoved. In step (B) of this invention, water is sometimes entrained in the unreacted aminating reagent during the course of its removal, and the liquid can be removed. This liquid will be referred to hereinafter as the recovered liquid.

According to one specific procedure of the operation of removing the unreacted aminating reagent, the temperature of the reaction mixture from which the unreacted aminating reagent has been removed is adjusted usually to 80° to 250° C., preferably 100° to 200° C., namely to a point equal to the reaction temperature or lower than it, and the pressure of the reaction system including the reaction mixture is released to thereby remove a greater portion of the unreacted aminating reagent. The pressure of the reaction system upon the termination of the pressure releasing operation can usually be set at 0 to 10 kg/cm$^2$-G. In the process of this invention, the pressure is preferably set at 0 to 5 kg/cm$^2$-G in view of the subsequent operation.

The mixture composed of the unreacted aminating reagent removed from the reaction mixture by the above operation and water entrained in it can then be conducted to a stripper. At this time, the mixture is cooled to a temperature of usually 30° to 100° C., preferably 50° to 98° C., and the recovered aminating reagent is separated as a vapor phase and the recovered liquid, as a liquid phase. The recovered liquid may sometimes contain some amount of the aminating reagent dissolved therein, but it is not particularly detrimental. This gas-liquid separating operation is usually carried out under atmospheric pressure, but as required, under suitable elevated pressures. The recovered aminating reagent may be recycled to the aminating step (A) and can be re-used as the starting material.

In step (B), the reaction mixture from which the aminating reagent has been removed is then cooled to extract the crude aminophenol. At this time, it is especially preferred to add the washing mother liquor obtained in step (E) to the reaction mixture. This brings about the advantage that the ratio of the desired aminophenol to be recovered can be increased, and the temperature and concentration of the reaction mixture to be subjected to crystallization can be very easily adjusted.

Specifically, the washing mother liquor obtained in step (E) and kept at a low temperature is added to the aforesaid aminating agent-removed reaction mixture having substantially the same temperature as the reaction mixture, and the temperature of the resulting reaction mixture to be subjected to crystallization is set usually at 50° to 100° C., preferably at 65° to 90° C. The amount of the washing mother liquor added at this time is usually 10 to 500 parts by weight, preferably 10 to 50 parts by weight, per 100 parts by weight of the aminating reagent-removed reaction mixture. If required, the temperature of the mixture can be forcibly lowered to the aforesaid set temperature by, for example, blowing an inert gas into the reaction mixture to be subjected to crystallization. If required in the above operation, a suitable amount of water may be added to the aminating reagent-removed reaction mixture to be subjected to crystallization. Thereafter, the reaction mixture to be subjected to crystallization which has been made uniform by thorough stirring is cooled at a cooling rate of usually 0.001° to 1° C./min., preferably 0.01° to 0.5° C./min., and finally to 0° to 50° C. usually, preferably 25° to 45° C. Consequently, the mixture turns to a crystallization mixture containing the precipitated crude aminophenol.

In step (C) of the process of this invention, the crystallization mixture is separated into the crude aminophenol crystals and the reaction mother liquor containing the catalyst dissolved therein. The separation may be carried out, for example, by decantation, usually filtration through a filter made of a plastic or metallic mesh, or centrifugal filtration. The temperature at the time of separating operation is usually 0° to 40° C., preferably 10° to 35° C.

In step (D) of the process of this invention, the reaction mother liquor obtained in step (C) is partly or wholly recycled to the aminating reaction step (A). As a result, the recovered catalyst contained in the reaction mother liquor, which sometimes also contains small amount of unconverted dihydric phenol, can be recycled to the reaction for re-use.

With reference to the recycles, the step (A) will again be described. In the aminating reaction step (A) in this invention, the dihydric phenol and the aminating reagent are heated in the presence of water and the water-soluble catalyst to perform amination. At this time, the unreacted aminating reagent removed in step (B) may sometimes be recycled to step (A), and the mother liquor containing the catalyst and the unreacted dihydric phenol separated in step (C) is sent to step (A) by step (D).

Accordingly, the amounts of the dihydric phenol, aminating reagent and catalyst to be charged in step (A) are prescribed so as to satisfy the aforesaid conditions by considering the amounts of the recycles. With regard to the catalyst, the catalyst is sometimes lost during the operations in all of the steps of the process of this invention. Accordingly, even if all the reaction mother liquor separated in step (C) is recycled to step (A), not all of the catalyst used in the reaction is recovered and recycled to the aminating reaction step. The loss of the catalyst in this case is usually very little, but generally, the catalyst is additionally supplied in an amount corresponding to the loss, and as required, the amount of the additional catalyst can be properly selected within a range which meets the charging conditions. With regard to the aminating reagent, a greater portion of the unreacted aminating reagent is recovered by step (B), and recycled to the aminating step (A). A part of the unreacted aminating agent is also recycled to the aminating reaction step (A) as dissolved in the reaction mother liquor via step (D). Hence, a high recovery ratio of the unreacted aminating reagent can be achieved.

The amount of the aminating reagent to be additionally supplied in the aminating reaction is selected so as to satisfy the aforesaid charging conditions as in the case of the catalyst. Although the unreacted dihydric phenol remaining in the reaction mixture is usually little, it is recovered as dissolved in the reaction mother liquor by step (D) and recycled to step (A). In performing the next aminating reaction, therefore, the dihydric phenol is additionally supplied in an amount corresponding to the consumption as prescribed as in the case of the aminating reagent. The solvent may be added, as required, in amounts which satisfy the aforesaid charging conditions.

In step (E) of the process of this invention, the crude aminophenol crystals obtained in step (C) are washed with a washing liquor to obtain washed crude aminophenol crystals and a washing mother liquor, and thereafter, the aminophenol is separated from the washed crude aminophenol crystals and purified. Preferably but not essentially, the washing mother liquor is sent to step (B) and added to the aminating reagent-removed reaction mixture, as stated hereinabove.

Step (E) will now be described in detail. In performing the operation of washing the crude aminophenol crystals, the temperature of the washing system including the washing liquor is prescribed usually at 0° to 50° C., preferably at 25° to 45° C. As required, the pressure may be prescribed at an elevated or reduced pressure. Desirably, the washing operation is carried out in an atmosphere of an inert gas such as nitrogen. Preferably, the reaction solvent recovered in step (B) is used as the washing liquor in this invention. As required, fresh water or a liquor prepared by adding a suitable amount of fresh water to the recovered liquid can be used as the washing liquor.

Specifically, the washing operation is carried out as follows in accordance with the process of this invention. First, the crude aminophenol crystals are washed with the washing liquor. This can be carried out, for example, by holding the crude aminophenol crystals on a filter and sprinkling the washing liquor onto them, or by adding the crude aminophenol crystals to the washing liquor, stirring the mixture for a suitable period of time, and then separating the crystals by filtration or the like. The washed crude aminophenols may, as required, be washed further with a suitable amount of water or a mixture of the recovered liquid with water. The washing operation in this case is desirably carried out after washing the crude aminophenol crystals with the recovered liquid.

The amount of the washing liquid to be used in the washing operation is usually 10 to 1000 parts by weight, preferably 10 to 1000 parts by weight, per 100 parts by weight of the crude aminophenol crystals.

After the washing of the crude aminophenol crystals is over, a greater portion of the washing mother liquor adhering to the washed crude aminophenol crystals is removed by an ordinary method, for example by shaking it off using a centrifugal separator to give a cake of the washed crude aminophenol crystals. The treatment of removing the adhering washing mother liquor is not limited to the case mentioned, but can be carried out at any time a required numbers of times during the washing of the crude aminophenol crystals with the washing liquor. The washing mother liquor obtained by the washing operation may be recycled to step (B) for re-use.

In step (E) of the process of this invention, the washed crude aminophenol crystals can be purified by treating them by a method of distillation followed by recrystallization. The procedure of these treatments will be described below. The washed crude aminophenol crystals obtained in step (E) are distilled under reduced pressure in an atmopshere of an inert gas such as nitrogen to remove traces of the catalyst and high-boiling condensation products remaining therein. The distillation usually gives an aminophenol having an aminophenol content of at least 90% by weight. The aminophenol may sometimes contain small amounts of phenylenediamines and at times a trace of the unreacted dihydric phenol as impurities. The amount of other impurities is only trace and can actually be ignored. The distillation is desirably carried out at a pressure of 0.1 to 600 mmHg, preferably 1 to 500 mmHg, and a temperature of usually 120° to 250° C., preferably 140° to 220° C. The distillation can be carried out batchwise or continuously. The distillation bottom obtained by the distillation contains a small amount of the catalyst in addition to high-boiling condensation products. When the catalyst contains a metal component, the distillation bottom is burnt to remove the organic matter, and the catalyst can be recovered as metal oxide. For example, when the catalyst used is of a molybdic acid type, it may be recovered as molybdenum oxide and can be directly used as an additional supply of catalyst in the aminating step (A).

Recrystallization of the crude aminophenol obtained by distillation in the present invention gives high purity aminophenols. Desirably, the recrystallization operation in the process of this invention is carried out in an atmosphere of an inert gas such as nitrogen. Examples of a recrystallization solvent that can be used in the recrystallization operation include water, methanol, ethanol, methyl isobutyl carbinol and ethyl acetate. The use of water is preferred in view of the purity of the aminophenol and economy. The recrystallization solvent may be a mixture of, for example, the above-exemplified compounds. The amount of the recrystallization solvent used is usually 50 to 1000 parts by weight, preferably 100 to 500 parts by weight, per 100 parts by weight of the aminophenol to be recrystallized. According to the process of this invention, the aminophenol to be recrystallized is dissolved uniformly in the recrystallization solvent, and then the temperature of the solution is lowered to precipitate the aminophenol. The temperature conditions in this procedure are such that prior to the precipitation of the crystals, the solution of the aminophenol in the recrystallization solvent is maintained usually at 60° to 100° C., preferably 70° to 90° C., and then cooled at a rate of usually 0.01° to 1° C./min., preferably 0.01° to 0.5° C., and finally kept usually at 0° to 50° C., preferably at 25° to 45° C. The aminophenol crystals precipitated by the above procedure are separated from the recrystallization mother liquor by an ordinary method such as filtration. As required, the collected recrystallization mother liquor is removed, and the aminophenol crystals may further be washed with a suitable amount of a fresh supply of the recrystallization solvent. The wet aminophenol crystals having the recrystallization solvent adhering thereto are, for example, dried under reduced pressure to remove the recrystallization solvent to give a highly pure aminophenol as a final product.

The recrystallization mother liquor is usually concentrated and filtered to separate it into a filtrate and secondary crystals. The crystals may be sent to the distillation step and distilled together with the washed crude aminophenol crystals. On the other hand, the filtrate is discarded, or as required may be sent in a suitable amount to the distillation step and treated in the same manner as in the case of the crystals. Alternatively, a suitable amount of the recrystallization mother liquor may be removed out of the system, and the remainder may be distilled in the distillation step. On the other hand, the recrystallization washing liquor left after washing the precipitated aminophenol is recycled and re-used as the recrystallization solvent for preparing the recrystallization solution. When the reaction solvent used in this invention is water and the recrystallization solvent is also water, water which distills out from the top during the distillation in the distillation step may be used as a fresh recrystallization solvent or a washing liquor for the precipitated aminophnenol.

In the recrystallization operation in step (E) of the present invention, a very small amount of such an additive as sodium thiosulfate, sodium dithionite, sodium sulfite, sodium hydrogen sulfite or sodium sulfide may be added to the recrystallization solution in order to stabilize the aminophenol. The amount of the additive is usually 0.001 to 5 parts by weight, preferably 0.05 to 1 part by weight, per 100 parts by weight of the recrystallization solution.

The aminophenol crystals as washed are wet with the adhering recrystalization solvent. Upon removal of the solvent by drying, an aminophenol having a purity of at least 99.5% can be obtained.

The process for producing the aminophenol in accordance with this invention is specifically described by way of example with reference to the accompanying drawing, FIG. 1, which illustrates the process for producing an aminophenol by a continuous method. The aminating step (A) is carried out in a reactor 1. The reaction mixture obtained in the aminating step (A) is sent to a flash tower 2. From the top of the tower, the unreacted aminating reagent and water entrained in it are withdrawn, and the aminating reagent-removed reaction mixture is withdrawn from its bottom. The materials withdrawn from the top of the tower are introduced into a gas-liquid separator 3, and the gas separated there is returned as the unreacted aminating reagent a to the aminating step (A). The separated liquid is sent as the recovered liquid b to a filtration-washing device 5. At this time, a suitable amount of water h may be added to the recovered liquid b. On the other hand, the aminating reagent-removed reaction mixture withdrawn from the bottom of the flash tower 2 is sent to a crystallization tank 4. At this time, it is preferred that the washing mother liquid d formed in the step of the filtration-washing device 5 be sent to the flash tower 2, and the aminating reagent-removed reaction mixture is conveyed to the crystallization tank 4 while being washed with the mother liquor d. As required, a part of the washing mother liquor d may be directly sent to the crystallization tank 4. The reaction mother liquor c containing the catalyst which is formed in the filtration-washing device 5 is returned to the reactor 1 for the amination step, and supplemented with required amounts of the dihydric phenol k, the aminating reagent l, and the additional catalyst m. The amination reaction is again carried out.

The washed crude aminophenol crystals from the filtration-washing device 5 are sent to a distillation column 6, withdrawn as a crude aminophenol from the top of the column, and fed to a recrystallization tank 7. Water is withdrawn from the top of the column 6, and the distillation bottom j is withdrawn from its bottom. The aminophenol crystals obtained in the recrystallization tank are fed into a filtration-washing device 8, and dried in a dryer 10 to give an aminophenol as a final product n. In the filtration-washing device 8, a recrystallization solvent g is added, and the recrystallization washing liquor f formed in the washing device 8 is recycled to the recrystallization tank 7. The recrystallization mother liquor e formed in the washing device 8 is sent to a secondary recrystallization tank 9. A suitable amount of the secondary recrystallization mother liquor obtained here is removed as a waste liquor i, and the remainder is recycled to the distillation column 6. If desired, the recrystallization mother liquor e may be partly discharged as the waste liquor i, and the remainder may be recycled to the distillation column 6 without going through the secondary recrystallization tank 9.

As is clear from the foregoing statement, when the process of this invention is applied to the industrial production of aminophenols, highly pure aminophenols can be produced economically advantageously without any significant losses of the catalyst and the unreacted aminating agent by simpler process steps than in a conventional process.

The following Examples illustrate the process of this invention in greater detail. All parts and percentages in these examples are by weight unless otherwise specified.

EXAMPLE 1

A SUS 316 stainless steel autoclave was charged with 110 parts of resorcinol, 194 parts of 27.5% aqueous ammonia and 35 parts of ammonium paramolybdate $[(NH_4)_6Mo_7O_{24} \cdot 4H_2O]$ as a catalyst under a nitrogen atmosphere, and the reaction was carried out at 200° C. for 6 hours with stirring. A this time, the pressure decreased to 22 kg/cm$^2$-G from 33 kg/cm$^2$-G.

After the reaction, the reaction mixture was transferred to a flash tower, and its temperature was lowered to 140° C. While the reaction mixture was maintained at this temperature, the pressure was released to remove ammonia from the reaction mixture. By this operation, 93.7 parts of a mixture of ammonia and water entrained was removed. The mixture flash-removed was conducted to a stripper and separated at 95° C. into 32.2 parts of ammonia gas and 61.4 parts of an aqueous solution containing small amount of ammonia (to be referred to as the recovered solution) which were respectively recovered.

The reaction mixture left after the ammonia removing operation was transferred to a crystallization tank while being washed with 66 parts of water, and then kept at a temperature of 65° C. The mixture was sufficiently stirred so as to form a uniform solution. By cooling the solution to 30° C. over 4 hours, a crystallization mixture containing precipitated meta-aminophenol crystals was obtained. The crystallization mixture was centrifugally filtered by using a 100-mesh basket to separate it into crude meta-aminophenol crystals and the reaction mother liquor. The amount of the resulting reaction mother liquor was 192.3 parts. The crude meta-aminophenol crystals obtained were further washed under centrifugation with all of the recovered solution mentioned above to obtain 91.3 parts of washed crude meta-aminophenol crystals in the form of a wet cake and 54.2 parts of the washing mother liquor.

The washed meta-aminophenol crystals were subjected to simple distillation at 160° C. and 7 mmHg to give 78.9 parts of crude meta-aminophenol as a distillate. The amount of the distillation residue was 2.4 parts, and the amount of the distillate was 8.0 parts.

To the meta-aminophenol obtained by distillation was added 94.7 parts of water containing 0.4% of sodium dithionite, and the mixture was heated at 80° to 85° C. to prepare a recrystallization aqueous solution of meta-aminophenol. The aqueous solution was cooled with stirring to 40° C. over 4 hours, and the resulting crystallization mixture was centrifugally filtered through a 100-mesh basket to give meta-aminophenol crystals and 98.5 parts of the recrystallization mother liquor. The meta-aminophenol crystals were washed under centrifugation with 36.8 parts of water, and dried to give 68.9 parts of meta-aminophenol having a purity of 99.8%.

In the reaction of this example, the conversion of resorcinol was 93.8 mole %, and the selectivity of meta-aminophenol was 90.5 mole %.

EXAMPLE 2

80.9 parts of resorcinol, 0.75 part of ammonium paramolybdate, the recovered ammonia gas obtained in Example 1, and 15.9 parts of a fresh supply of ammonia gas were added to 150.7 parts of the reaction mother liquor obtained in Example 1, and the mixture was reacted. In the aminophenol distillation step, the secondary crystals obtained from the recrystallization mother liquor in Example 1 were added to the washed meta-aminophenol crystals obtained in this example and distilled together. Furthermore, in the preparation of the recrystallization aqueous solution, the recrystallization washing mother liquor and the distillate obtained in Example 1 were used instead of water.

Otherwise, the reaction and work-up were carried out under the same conditions and by the same method as in Example 1 to give 69 parts of meta-aminophenol having a purity of 99.8%.

In the reaction of Example 2, the conversion of resorcinol was 99.1 mole %, and the selectivity of meta-aminophenol was 91.2 mole %, as calculated on the basis of the resorcinol that was added as a supplement. The total yield of meta-aminophenol at this time was 86 mole % based on the charged resorcinol.

What is claimed is:

1. A process for producing an aminophenol, which comprises
   (A) a step of reacting a dihydric phenol with an aminating reagent in the liquid state under heat in the presence of water and a water-soluble catalyst,
   (B) a step of removing the unreacted aminating reagent from the reaction mixture, and then precipitating th crude aminophenol from the reaction mixture from which the aminating reagent has been removed, thereby to obtain a crystallization mixture containing the crude aminophenol,
   (C) a step of separating the crystallization mixture into crystals of the crude aminophenol and the reaction mother liquor containing the catalyst,
   (D) a step of circulating part or the whole of the reaction mother liquor to the aminating step, and (E) a step of washing the crude aminophenol crystals with a washing liquor to obtain the washed crude aminophenol crystals and the washing mother liquor, and thereafter separating the aminophenol from the washed crude aminophenol crystals and purifying it.

2. The process of claim 1 wherein the solution containing water which is entrained in the unreacted aminating reagent when the unreacted aminating reagent is removed from the reaction mixture in step (B) is used as the washing liquor for the crude aminophenol crystals in step (E).

3. The process of claim 1 wherein the washing mother liquor obtained in step (E) is added to the aminating agent-removed reaction mixture in step (B), and thereafter the crude aminophenol is precipitated in step (B).

4. The process of claim 1 wherein the unreacted aminating reagent removed and recovered from the reaction mixture in step (B) is recycled to step (A) as part of the starting material.

5. The proces of claim 1 wherein in separating the aminophenol from the washed aminophenol crystals and purifying it in step (E), the washed aminophenol crystals are distilled to give a crude aminophenol, and the crude aminophenol is recrystallized to give a pure aminophenol.

6. The process of claim 5 wherein the crude aminophenol is recrystallized using water as the recrystallization solvent.

7. The process of claim 1 wherein the dihydric phenol is resorcinol or hydroquinone and the aminating reagent is ammonia.

8. The process of claim 7 wherein step (A) comprises reacting resorcinol with ammonia at a temperature of from 170° to 350° C. and a pressure of from 5 to 150 kg/cm$^2$ in the pressure of 10 to 1000 parts by weight, per 100 parts by weight of resorcinol, of water, and a water soluble ammonium salt catalyst to obtain an aqueous reaction mixture containing crude aminophenol, unreacted resorcinol, unreacted ammonia, reaction by-products, catalyst and water, and step (B) comprises removing unreacted ammonia from the aqueous reaction mixture containing crude aminophenol, adding aqueous washing mother liquor obtained from step (E) to the ammonia depleted aqueous reaction mixture and thereafter cooling the resulting mixture to precipitate crude aminophenol as crystals of crude aminophenol to thereby obtain an aqueous crystallization mixture containing crude aminophenol.

* * * * *